United States Patent [19]

Whitehead et al.

[11] Patent Number: 5,316,937
[45] Date of Patent: May 31, 1994

[54] CONDITIONED MEDIUM USEFUL FOR SUSTAINING GROWTH OF COLONIC CRYPT CELLS

[75] Inventors: R. H. Whitehead; Anthony Burgess; Hui-Hua Zhang, all of Victoria, Australia

[73] Assignee: Ludwig Institute for Cancer Research, N.Y.

[21] Appl. No.: 851,732

[22] Filed: Mar. 16, 1992

[51] Int. Cl.$^5$ .................................. C12N 5/00
[52] U.S. Cl. .................. 435/240.3; 435/240.2; 435/70.3
[58] Field of Search ............ 435/240.3, 240.31, 70.3, 435/240.2, 240.21

[56] References Cited

PUBLICATIONS

Whitehead et al, In Vitro Cell & Dev. Biology, 23 (6), pp. 436–442, Jun. 1987.
Whitehead et al, Int. J. Cancer, 46, pp. 858–863, 1990.
Nice et al, J. of Biological Chemistry, 266 (22), pp. 14425–14430, Aug. 5, 1991.
ATCC Catalogue of Cell Lines & Hybridomas, 6th edition, 1988, p. 354.

*Primary Examiner*—Douglas W. Robinson
*Assistant Examiner*—Susan M. Dadio
*Attorney, Agent, or Firm*—Felfe & Lynch

[57] ABSTRACT

The invention describes a colonic crypt cell stimulating mitogen, and conditioned medium containing it. In particular, cell line LIM 2537 is described which, when cultivated in medium, secretes a mitogen which stimulates the proliferation o colonic crypt cells. Applications of the conditioned medium and the cell line are also described.

3 Claims, 4 Drawing Sheets

CONDITIONED MEDIUM USEFUL FOR SUSTAINING GROWTH OF COLONIC CRYPT CELLS

FIELD OF THE INVENTION

This invention relates to a factor useful as a stimulator of colon crypt cells. More particularly, it relates to a factor identified as a mitogen which is produced by a colonic cell line, and conditioned medium containing it.

BACKGROUND AND PRIOR ART

Many cell products have been identified via analysis of their effect on targeted cell populations and subpopulations. Such products include a plethora of materials including growth factors, cytokines, and so forth. These substances are extremely powerful and are produced in vanishingly small amounts by normal cells.

One of the major goals of contemporary molecular biology is the identification and cloning of genes which produce the various materials generally discussed supra. While such genes have been identified for materials such as erythropoietin (see, e.g., U.S. Pat. No. 4,703,008), and interleukin-7 (see, e.g., U.S. Pat. No. 4,965,195), the relevant genetic material is not always available, or is not available as quickly as the art would like. In such cases, an important means of securing sufficient amounts of the material of interest is via the identification and isolation of cell lines which produce the desired product.

Examples of proteinaceous cell products which were first identified via cell lines which produced them are "granulocyte colony stimulating factor" or "G-CSF" (see U.S. Pat. No. 4,833,127), and interleukin-3 (see U.S. Pat. No. 4,658,018). The latter patent is of particular interest because, while the factor could not be completely characterized in terms of parameters such as molecular weight, isoelectric point, etc., its functional properties were clearly defined. Another example of this approach to factors of biological pertinence and their isolation from cell lines may be seen in Golde et al., U.S. Pat. No. 4,438,032. Of course, the artisan is also aware of the vast number of known monoclonal antibodies which are produced by hybridoma cell lines. Frequently, the most pertinent feature of these proteins is their specificity, and this is all that is required to identify them.

Although many factors involved in the formulation of cell growth have been identified, the diversity of different cell types is evidence of the need to continue work toward identifying and characterizing factors which have specific targets, i.e., which stimulate particular cell types.

The different cell types of a mature organism do not appear "sua sponte", rather, they develop from precursor cells which have the ability to differentiate into different types of mature cells. These precursor cells are referred to as "stem cells" generally, and are an important resource to the field for studies on cellular development. The importance of stem cells to basic research can be seen in U.S. Pat. No. 5,061,620, to Tsukamoto et al., which involves the isolation and maintenance of hematopoietic stem cells. Various media, including IMDM, and RPMI are described as growth media which can be used to maintain these stem cells.

The stem cells which develop into colonic mucosa are also referred to as colon crypt cells. While it has been possible to isolate these cells from mixed culture, their cultivation has been difficult. See in this regard Whitehead et al., In Vitro Cellular and Developmental Biology 23(6): 436–442 (1987), hereinafter referred to as "In Vitro", the disclosure of which is incorporated by reference. The methodology described therein requires, inter alia, the use of collagen gels and feeder layers of bovine aortic cells for extended culture of the crypt cells. This methodology is involved, and not completely satisfactory for the cultivation of colonic crypt cells.

Tumor cells are frequently the source of cell lines which are high producers of stimulatory factors for their normal counterparts. With reference to the patent literature cited supra, e.g., the cell lines identified as producers of G-CSF and IL-3, e.g., were isolated from tumorous material.

Cell lines derived from colon tumors and which can be traced to colonic crypt cells are known, as per, e.g., Whitehead et al., JNCI 74(4): 759–762 (1985), the disclosure of which is incorporated by reference and which described cell line LIM 1215, whose origin is traced to colon crypt cells. Not all cell lines produce pertinent factors, however, and there is no guarantee or pattern as to which cell lines will produce a stimulatory factor.

Investigations have now yielded a cell line which produces a factor not otherwise recognized by the art, and which acts as a mitogen on colonic crypt cells. The factor acts as a mitogen in that it stimulates DNA synthesis and proliferation of the targeted cells (i.e., colon crypt cells). The factor is secreted by the producing cell line into growth medium, to yield a conditioned medium which stimulates proliferation of colonic crypt cells. It is thus mitogen, the cell line producing it, and applications thereof, which are the subject of the invention described herein.

DETAILED DESCRIPTION OF THE PREFERRED EMBODIMENTS

Example 1

The cell line LIM 2537 was established from a biopsy taken from a human colon tissue sample.

A polyp lying adjacent to a colonic carcinoma in the rectum was observed to possess unusual features in that an excess number of nerve fibers and blood vessels were observed.

A portion of the polyp was used to establish cultures following the protocols described by Whitehead et al., JNCI, supra, the disclosure of which is incorporated by reference. After about two months of slow growth in culture, a small cell variant was noted which overgrew all cells in the culture. These cells were passaged, and stored in liquid $N_2$ at a low passage level. In addition, they were capable of growth in RPMI 1640 containing 5% fetal calf serum (FCS), and can be passaged using a trypsin-EDTA solution. Cells grew loosely attached as small spindle shaped cells with numerous rounded cells either loosely attached or floating in medium. The clones also grew in semi-solid agar using standard techniques. Cloning efficiency increased markedly as cell concentration increased, indicating an autocrine effect.

Studies showed that the cells grew readily as xenografts in nude mice, forming palpable tumors within 19 days. The cells are aneuploid, having about 55-60 chromosomes. They stain with anti-keratin monoclonal antibody LE-61, indicating they are of epithelial origin. They do not stain with anti-mucin antibodies or with antibodies to brush border marker other than aminopeptidase N.

A cell line has been established from the described culture, and has been named LIM 2537. A deposit of the cell line has been made in accordance with the Budapest Treaty. The deposit was made on Apr. 8, 1993 at the European Collection of Animal Cell Cultures (the "ECACC"), PHLS Centre for Applied Microbiology and Research, Portion Down, Salisbury Wlts, SP4 CJG, United Kingdom. The deposit has been accorded accession number 92040804.

EXAMPLE 2

The autocrine effect observed supra indicates that some factor was produced by the cells and secreted into the medium. As such, conditioned medium was prepared and then used in subsequent tests, described infra.

A sample of LIM 2537 cells were grown to 75% confluency, following the cultivation protocol described supra. Medium was then changed to RPMI 1640 plus 2% fetal calf serum (FCS), and followed by incubation for 48 hours at 37° C. Medium was collected, filtered through a $0.22\mu$ sterile filter, and stored at $-70°$ C. until tested.

EXAMPLE 3

The effect of the conditioned medium described in Example 2 on colonic crypt cells was tested.

A piece of normal colonic mucosa was washed and sterilized by soaking in a 0.1% solution of sodium hypochlorite in phosphate buffered saline (PBS) for 20 minutes at room temperature. Colonic crypt cells were then removed by using a solution containing 3 mM EDTA plus 0.5 mM DTT, as described by Whitehead et al., In Vitro 23: 436–442 (1987).

The mucosa was incubated for 90 minutes at room temperature, the EDTA mixture removed, an PBS was then added. The resulting mixture was then shaken vigorously to free crypts from the remaining tissue. This step was repeated until the yield of crypts decreased. The resulting crypt suspension was centrifuged gently, and the crypts were suspended in RPMI 1640 plus 5% fetal calf serum. Crypt concentration was adjusted to 300 crypts per ml, and the suspension aliquoted into wells of 24 well culture dishes, in 1 ml volume.

The LIM 2537 culture medium described supra was thawed and added to labelled wells at concentrations of from 2.5% to 20% (v/v), followed by incubation at 37° C. for 48 hours. Tritiated thymidine was then added to the wells at a concentration of 1 Curie per well, and incubation continued for another 6 hours. The cells' DNA was harvested on glass fiber paper using a commercial harvester, and the papers were then placed in a liquid scintillation vial, to which scintillation fluid was added. Vials were counted in a liquid scintillation counter, and tritiated thymidine incorporation equal to at least twice that of tube background wa considered indicative of background activity.

Figure 1:
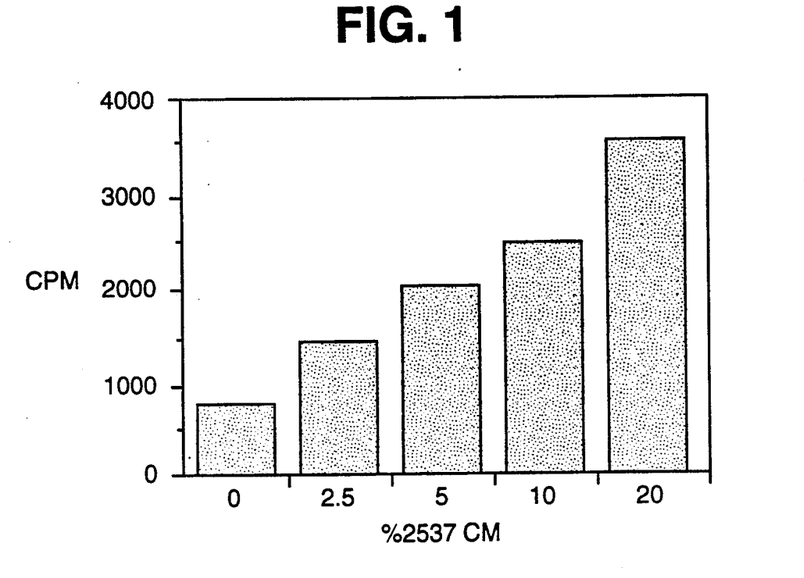
FIG. 1 shows incorporation of radiolabelled thymidine into human colon crypt cells, when cultured in the presence of mitogen from LIM 2537.

The results obtained are shown in FIG. 1. It is clear from these data that the conditioned medium contains a factor which is stimulating the proliferation of colonic crypt cells in a concentration dependent manner.

EXAMPLE 4

The experiments set forth in Example 3 involved human crypt cells. Parallel experiments were carried out, using colons from both new born and adult mice. Colons were removed from the mice, opened longitudinally, contents removed, and the colons were then washed in PBS, followed by the same steps set forth in Example 3.

Figure 2:
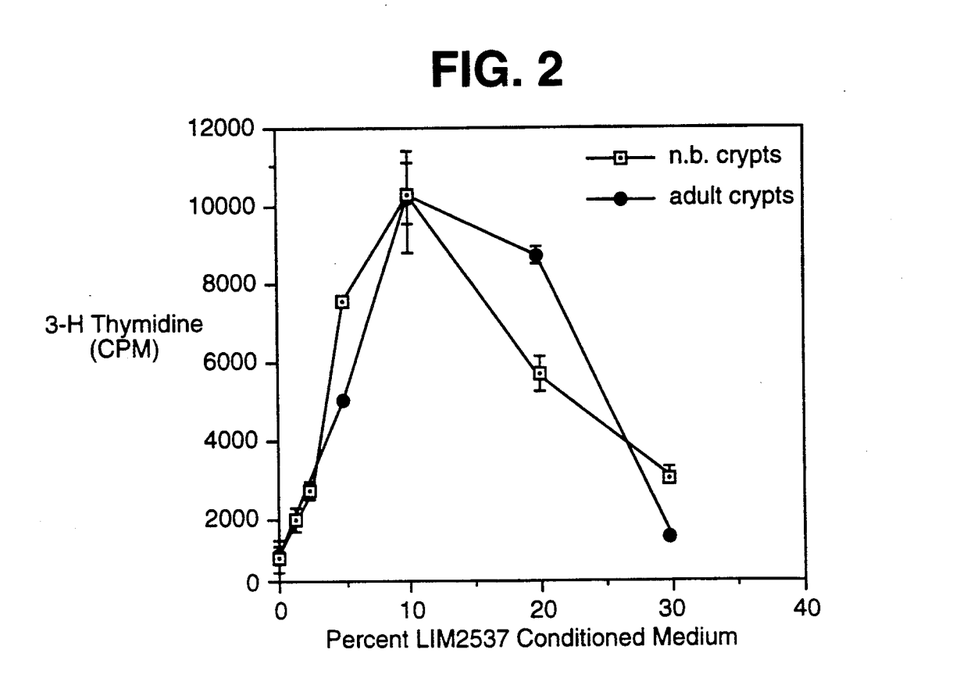
FIG. 2 depicts stimulation of murine colon crypt cells at various concentrations of conditioned medium containing the LIM 2537 mitogen.

FIG. 2 presents these results. It is noted that similar data were obtained with both newborn and adult colonic crypt cells.

EXAMPLE 5

Figure 3:
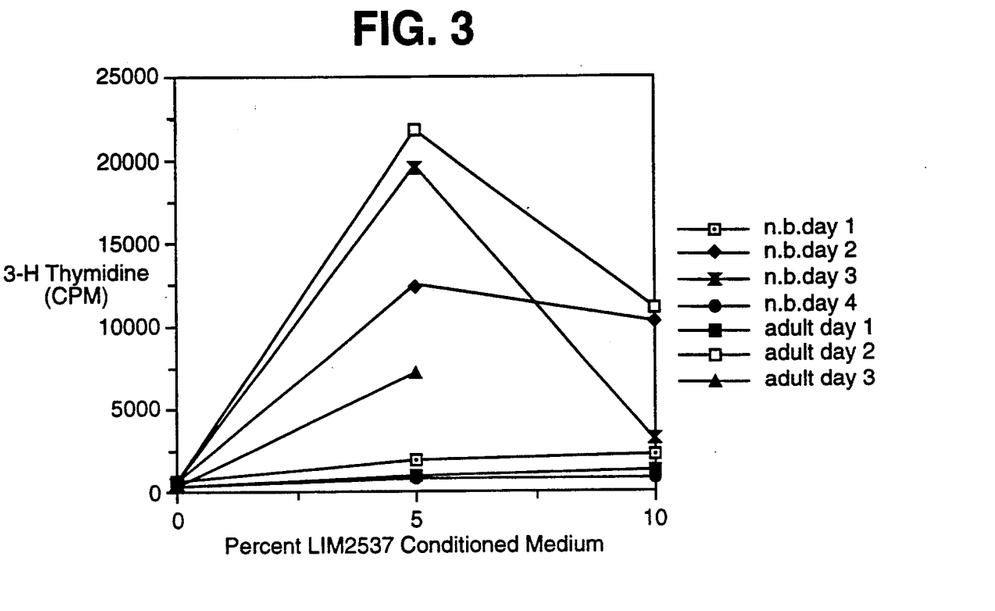
FIG. 3 presents results obtained when stimulation of murine colonic crypt cells in the presence of the mitogen was studied over time.

The same colonic crypt cell stimulation assay that was carried out in Example 4 was again performed, with the single exception that harvesting was after 48 hours. FIG. 3 sets forth these results, and indicates that while degree of stimulation varied from assay to assay, especially with respect to optional concentration of medium, the medium did induce DNA synthesis in the colonic crypt cells.

EXAMPLE 6

In another set of experiments, human colonic crypt cells were tested with conditioned medium from LIM 2537, together with different growth factors. Some of the growth factors tested included epidermal growth factor ("EGF"), fibroblast growth factor ("FGF"), interleukin 6 ("IL-6"), platelet derived growth factor ("PDGF"), gastrointestinal peptide "PPP", and glucagon. None of these factors showed any synergism with the LIM 2537 conditioned medium, when tested on murine colonic crypt cells.

EXAMPLE 7

Figure 4:
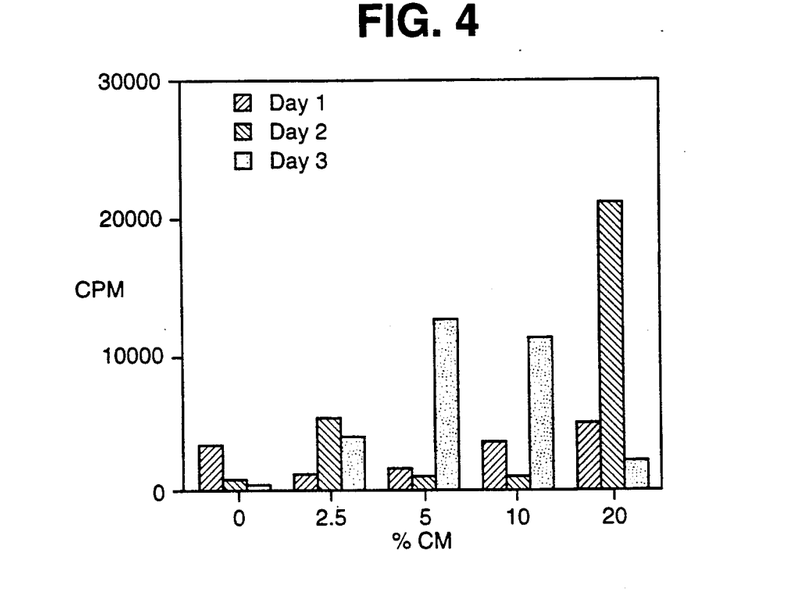
FIG. 4 shows the response of human colon crypt cells to LIM 2537 mitogen over time and at varying concentrations.

The response of human colonic crypt cells over time and at varying concentrations was also examined. FIG. 4 summarizes these results, which were secured using the thymidine incorporation assay described supra. Depending upon the concentration, stimulation was greatest on either the second or third day of culture; however, at all concentrations, the crypt cells were stimulated by the conditioned medium.

EXAMPLE 8

Colony formation using various factors was studied. Cells of cell line LIM 1215 were cloned in semi-solid agar (0.3%) following Whitehead et al., Int. J. Canc. 46: 858–863 (1990). Briefly, the cells were trypsinized and resuspended in RPMI 1640 plus 5% FCS. Cells in the suspension were counted and then resuspended in a mixture of 0.3% agar in RPMI 1640 plus 10% FCS (40° C.), at a concentration of $10^4$ cells per ml. The mixture was plated in 1.5 volumes in 35 mm² dishes, and allowed to set. Plates were then incubated at 37° C. in 5% $CO_2$ and 100% humidity for 14 days. Plates were stained with 0.1% crystal violet, and colonies of more than 40 cells were counted.

Conditioned medium was prepared by incubating confluent monolayers of colon carcinoma cell lines with fresh RPMI 1640 plus 5% FCS for 48 hours. Medium was then removed, sterilized by filtration, and added to the agar plates at a final concentration of 10% (v/v). Basic fibroblast growth factor ("bFGF"), and a crude pituitary fraction, referred to as "A2", were also tested. These materials had previously been shown to be active as colonic crypt cell growth factors. See Whitehead, supra.

Figure 5:
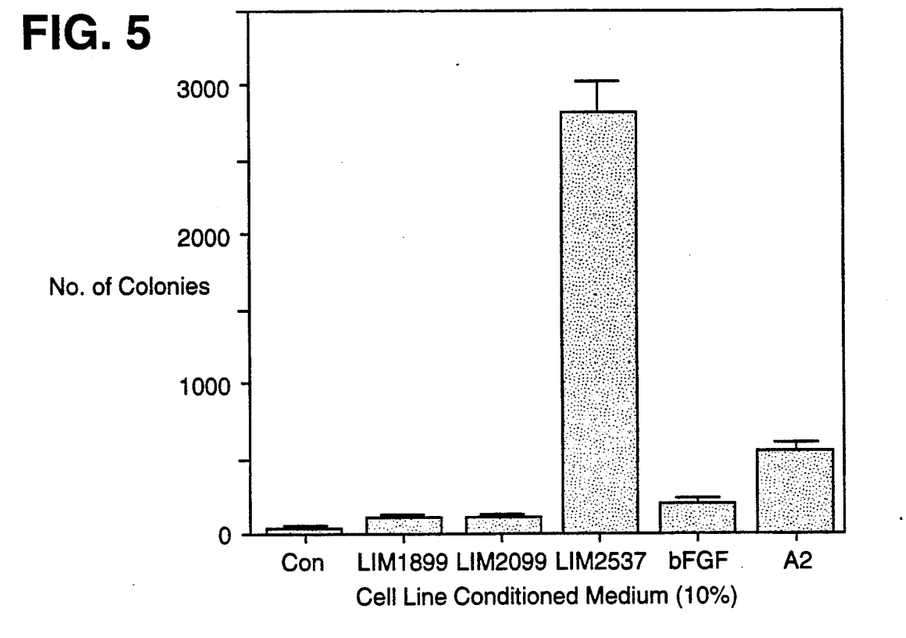
FIG. 5 shows data from a colony formation assay.

The results of these experiments are shown in FIG. 5. Note the vast superiority of the conditioned medium obtained from LIM 2537 as compared to other materials.

EXAMPLE 9

In another experiment, human colonic crypt cells were combined with an ammonium sulphate precipitate ("ASP") of the LIM 2537 conditioned medium.

Human crypts were isolated from colonic mucosa using 3 mM EDTA and 0.5 mM DTT, following Whitehead et al., In Vitro 23: 436–442 (1987). The crypt cells were resuspended in RPMI 1640 containing 2% FCS, and the concentration was then adjusted to 200 crypts per ml. The crypt suspension was aliquoted into the wells of 24 well plates in 1 ml volume. One hundred mls of conditioned medium was prepared from 48 hour cultures of LIM 2537, clarified by centrifugation, and ammonium sulphate was added to a final concentration of 30% (w/v). The mixture was allowed to stand for 4° C. overnight, and was then centrifuged. The supernatant was discarded, and the pellet resuspended in 10 mls of phosphate buffered saline (0.1M). The redissolved precipitate was added to crypts in doubling dilutions, starting at 2%. LIM 2537 conditioned medium was also tested after freezing for 48 hours in order to test stability. Crypts were cultured at 37° C. for 48 hours, and were then labelled by adding $^3$H-thymidine at a final concentration of $1\mu$/Ci per ml. Plates were reincubated for six hours, and the cells were harvested onto glass fiber filter mats. Amounts of incorporated radioactivity was determined in a liquid scintillation counter.

Figure 6:
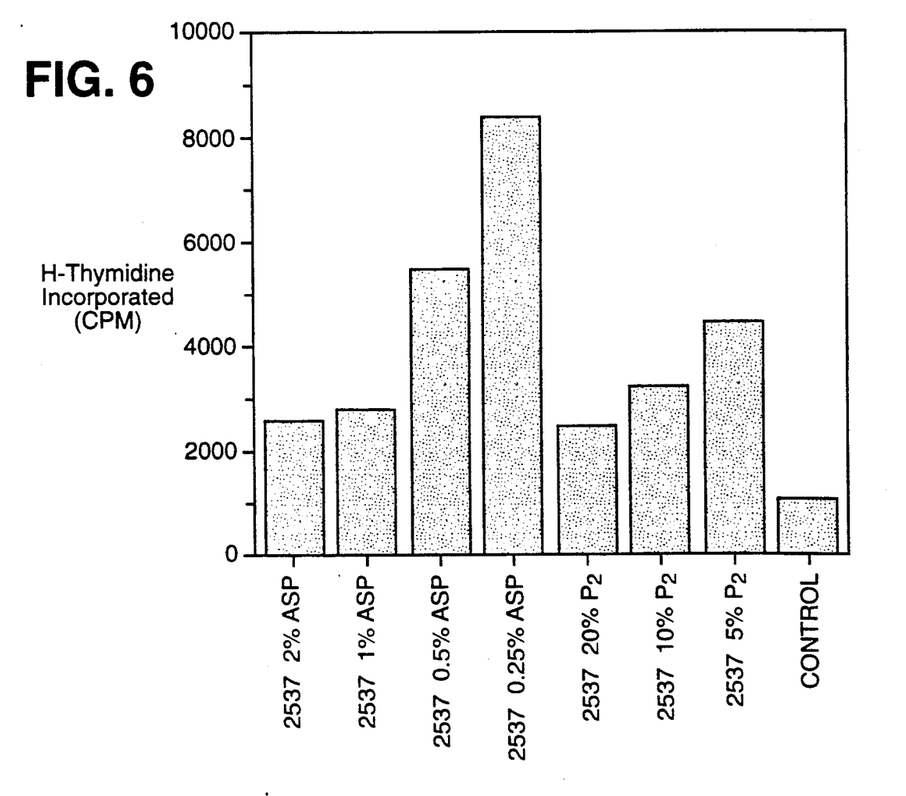
FIG. 6 compares LIM 2537 ammonium sulphate precipitates and frozen LIM 2537 conditioned medium at varying concentrations.

The results, shown in FIG. 6, depict the precipitate ("ASP") in the first four columns reading left to right, and the results with frozen material ("FZ") in columns 5–7, reading left to right. A control experiment is also shown. Again, the performance of the factor is clear.

EXAMPLE 10

A comparison was made among LIM 2537 conditioned medium, the precipitate, redissolved in PBS, or precipitate redissolved in TRIS.

Adult mice colonic crypt cells were isolated from colonic mucosa, and were plated in 24 well plates at 200 crypts per well in RPMI 1640 plus 2% FCS. Conditioned medium was added at concentrations of 5, 10 and 20%, and after precipitation with ammonium sulphate. The precipitated material was either redissolved in phosphate buffered saline (pH 7.2) or in PBS containing 20 mM TRIS (pH 7.2).

Figure 7:
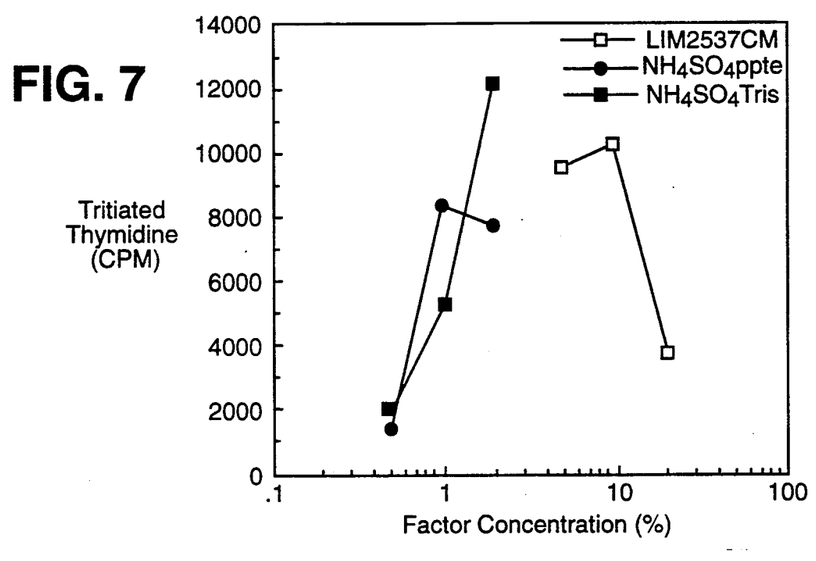
FIG. 7 displays data obtained from LIM 2537 conditioned medium, ammonium sulphate precipitate resuspended in phosphate buffered saline, and the resuspension with Tris buffer added.

FIG. 7 presents these results, with the TRIS solution clearly showing the best results.

The foregoing experiments demonstrate that cell line LIM 2537 produces a factor which is clearly mitogenic to colonic crypt cells. Further investigations have revealed that this factor is heat labile, and is only stable over a pH range of from 6 to 8.

The invention will be seen to relate to the colonic crypt mitogen produced by cell line 2537, as well as conditioned medium secured therefrom. "Conditioned medium" as used herein, refers to a mixture of a growth medium which sustains the growth of colonic cells, especially LIM 2537, and the colonic crypt cell mitogenic factor produced by LIM 2537. The medium used in the foregoing experiments included RPMI 1640 and 20% fetal calf serum, although it will be understood by the skilled artisan that various media can be used, as long as the source cell line LIM 2537 is capable of growth therein.

The conditioned medium described herein places in the hands of the artisan a method for growing colonic crypt cells, as well as a methodology for identifying these cells in culture. One simply adds a conditioned medium of the type described herein to a culture to be assayed, and monitors proliferation of cells. Said proliferation is indicative of the presence of colonic crypt cells in the sample. The methodology, in a preferred embodiment, utilizes some marker in connection with the medium, such as tritiated thymidine. Other markers, and other uses of the invention described herein, will be apparent to the skilled artisan.

The factor described herein may be used in e.g., therapeutic approaches designed to alleviate chemotherapeutic induced toxicity. In this respect, it parallels both G-CSF and GM-CSF ("granulocyte" and "granulocyte, macrophage" colony stimulating factor) in reversing damage to stem cells. The factor can also be used, either alone or in connection with other therapies following colostomy. One side effect seen in patients is atrophy of mucosal linings in by-passed segments. As the factor is a stimulator for the crypt cells, atrophy can be reversed.

The factor may also be used as an agent helpful in developing or screening "anti-factors". Several diseases of the colon, including Crohn's disease and ulcerative colitis, are characterized by hyperproliferation of colonic cells. In view of the identification of a crypt cell growth factor, various agents can be tested or developed which arrest or inhibit the effect of the factor. These may then be considered as potential therapies for those types of diseases characterized by hyperproliferation.

The factor may also be used as a therapy in conditions where colonic mucosa is compromised in some way. These conditions include short bowel syndrome, and they are characterized by a loss of ability to absorb nutrients, e.g.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A conditioned medium, useful for sustaining growth of colonic crypt cells, comprising a colonic crypt cell stimulating mitogen; said medium produced by culturing cell line LIM 2537 in a culture medium, wherein the cell line LIM 2537 produces said mitogen, and removing the cells of said cell line from the conditioned medium.

2. The conditioned medium of claim 1, wherein said culture medium is RPMI 1640.

3. The conditioned medium of claim 2, further comprising fetal calf serum.

* * * * *

UNITED STATES PATENT AND TRADEMARK OFFICE
CERTIFICATE OF CORRECTION

Page 1 of 2

PATENT NO. : 5,316,937
DATED : May 31, 1994
INVENTOR(S) : Whitehead et al.

It is certified that error appears in the above-indentified patent and that said Letters Patent is hereby corrected as shown below:

<u>IN THE ABSTRACT</u>

Line 5: change "o" to --of--

Column 1, line 67: change "a" to --as--

Column 2, line 20: change "described" to --describe--.
Column 2, line 33: change "thus" to --this--.
Column 2, line 56: change "the" to --then--.
Column 3, line 9: change "can" to --could--.
Column 3, line 59: change "an" to --and--.

UNITED STATES PATENT AND TRADEMARK OFFICE
CERTIFICATE OF CORRECTION

PATENT NO. : 5,316,937
DATED : May 31, 1994
INVENTOR(S) : Whitehead et al.

It is certified that error appears in the above-indentified patent and that said Letters Patent is hereby corrected as shown below:

Column 4, line 12: change "wa" to --was--

Column 6, line 56: change "108s" to --loss--.

Signed and Sealed this

Eighteenth Day of April, 1995

BRUCE LEHMAN

*Attest:*

*Attesting Officer*

*Commissioner of Patents and Trademarks*